(12) United States Patent
Liang et al.

(10) Patent No.: US 6,335,455 B1
(45) Date of Patent: *Jan. 1, 2002

(54) PROCESS FOR THE PRODUCTION OF 2,5-DIHYDROFURAN

(75) Inventors: Shaowo Liang, Kingsport, TN (US); Yao-Ching Liu, Longview, TX (US)

(73) Assignee: Eastman Chemical Company, Kingsport, TN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/141,592

(22) Filed: Aug. 28, 1998

Related U.S. Application Data

(60) Provisional application No. 60/071,162, filed on Jan. 12, 1998.

(51) Int. Cl.$^7$ .................. C07D 307/02; C07D 487/00
(52) U.S. Cl. ........................... 549/507; 549/469
(58) Field of Search .................. 548/429; 549/469, 549/507

(56) References Cited

FOREIGN PATENT DOCUMENTS

WO          91/13882          9/1991          ................. 549/469

OTHER PUBLICATIONS

Pereyre et al, Chemical Abstract vol. 70, No. 96884, Alkylation of Carbon Atoms α to Functional Groups by Organotin Reagents. (1969).*

* cited by examiner

*Primary Examiner*—John Kight
*Assistant Examiner*—Raymond Covington
(74) *Attorney, Agent, or Firm*—Harry J. Gwinnell; Michael J. Blake

(57) ABSTRACT

This invention pertains to a process for the preparation of 2,5-dihydrofurans by the isomerization of γ,δ-epoxyalkenes in the presence of a catalyst system comprising an organotin compound and an alkali metal iodide.

30 Claims, No Drawings

PROCESS FOR THE PRODUCTION OF 2,5-DIHYDROFURAN

This application claims priority under 35 U.S.C. §119(e) to U.S. Provisional Application No. 60/071,162 filed on Jan. 12, 1998.

BACKGROUND OF THE INVENTION

1. Field of the Invention

This invention pertains to isomerization processes and, more particularly, to processes whereby γ,δ-epoxyalkenes and γ,δ-epoxycycloalkenes are isomerized to obtain the corresponding 2,5-dihydrofuran compounds in the presence of a catalyst system comprising an organotin compound and an alkali metal iodide in the presence or absence of a solvent at a temperature of 50 to 200° C.

2. Description of the Related Art

Dihydrofurans are reactive heterocyclic species which are useful in a variety of applications, e.g., as intermediates in the production of useful polymers and chemicals. However, the use of dihydrofurans for such purposes has heretofore been restricted due to the non-availability of cost-effective preparative procedures.

U.S. Pat. Nos. 3,932,468 and 3,996,248 disclose the production of 2,5-dihydrofurans by the rearrangement of substituted or unsubstituted epoxyalkenes with a homogeneous catalyst system comprising hydrogen iodide or hydrogen bromide and a transition metal Lewis acid in an organic solvent. This process suffers disadvantages of the use of corrosive hydrogen halides, high level of oligomer formation, and complications in product isolation. We have found that the process of U.S. Pat. Nos. 3,932,468 and 3,996,248 also results in the unwanted production of up to 15% α,β-unsaturated aldehydes or ketones.

U.S. Pat. No. 5,034,545 describes a method for the isomerization of epoxyalkenes to 2,5-dihydrofurans, in the liquid phase, in the presence of a catalyst system containing an alkali or alkaline earth metal halide or an onium halide, a Lewis acid, and an organic solubilizer. The best reported results were attained by using the combination of a zinc halide and an alkali metal halide. We have found that such combinations of catalyst system described in U.S. Pat. No. 5,034,545 gave very poor catalyst lifetime. The catalyst activity and the reaction of the epoxide decrease considerably after a short operation time and result in a high level of oligomer formation. Therefore, this method is uneconomical.

Furthermore, U.S. Pat. No. 5,315,019 discloses the isomerization of epoxybutenes in the liquid phase, wherein organotin and a tetraalkylammonium or phosphonium iodide are used as the catalyst system. European Patent No. 0 691 334 A1 discloses a method for the rearrangement of epoxybutenes to 2,5-dihydrofurans, in the liquid phase, in the presence of a Lewis acid and a phosphazenium halide or a phosphazanium halide in an organic solvent. Catalysts used in these methods are expensive. Some of them are not readily commercially available. Moreover, relatively large quantities of catalysts must be used in order to obtain satisfactory yields and selectivities.

The invention under consideration was thus based on the task of finding a catalyst system for the isomerization of epoxybutenes to 2,5-dihydrofurans, which is free of the aforementioned disadvantages.

SUMMARY OF THE INVENTION

We have discovered a catalytic process with a novel catalyst system for the isomerization of γ,δ-epoxyalkenes to produce dihydrofurans. The process provides high levels of epoxyalkene conversion with high selectivity to the desired dihydrofuran product. Long catalyst lifetimes are realized and the product may be recovered by relatively simple means since the catalyst and reaction mixture are readily separated by such simple techniques as distillation, decantation, filtration, gas stripping methods, gas/liquid flow separation, and the like. Catalysts involved in the process of this invention are readily obtainable by simple synthetic preparations or are commercially available.

In accordance with the present invention, there is provided a process for the isomerization of γ,δ-epoxyalkenes to the corresponding 2,5-dihydrofuran compounds, which process comprises contacting a γ,δ-epoxyalkene or γ,δ-epoxycycloalkene with a catalytic amount of an organotin compound in combination with an alkali metal iodide to catalyze the isomerization process of our invention under isomerization conditions of temperature and pressure.

DETAILED DESCRIPTION OF THE INVENTION

The γ,δ-epoxyalkene and γ,δ-epoxycycloalkene reactants suitable for use in the process of our invention may contain from 4 to about 20 carbon atoms, preferably from 4 to about 8 carbon atoms. Examples of the epoxyalkene and epoxycycloalkene reactants include compounds having the structural formula (I):

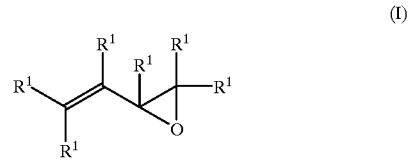

wherein each $R^1$ is independently selected from hydrogen, alkyl of up to about 8 carbon atoms, a carbocyclic or heterocyclic aryl group of about 5 to 10 carbon atoms or halogen, or any two $R^1$ substituents collectively may represent an alkylene group forming a ring, e.g., alkylene, containing in the main chain up to about 8 carbon atoms.

The preferred epoxyalkene reactants comprise compounds of formula (I) wherein only two of the $R^1$ substituents individually may represent lower alkyl, e.g., alkyl of up to about 8 carbon atoms, or collectively represent straight or branched chain alkylene of up to about 8 carbon atoms. Exemplary compounds contemplated for use in the practice of the present invention include 3,4-epoxy-3-methyl-1-butene, 2,3-dimethyl-3,4-epoxy-1-butene, 3,4-epoxycyclooctene, 3,4-epoxy-1-butene, 2,5-dimethyl-2,4-hexadiene monoepoxide, and the like. The epoxyalkene reactant of primary interest is 3,4-epoxy-1-butene.

The 2,5-dihydrofuran compounds obtained in accordance with our novel process have the structural formula (II):

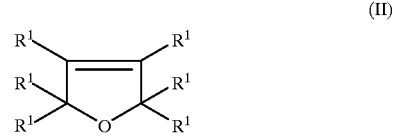

wherein the $R^1$ substituents are defined above. Of the compounds which may be obtained in accordance with our invention, the compound of primary interest is 2,5-dihydrofuran.

The preferred alkali metal iodides for use in the present invention include lithium iodide, sodium iodide, and potassium iodide. Lithium iodide and potassium iodide are particularly preferred.

The alkali metal iodide is used in combination with an organotin compound to catalyze the isomerization process of our invention. The organotin compound may be selected from organotin (IV) compounds such as hydrocarbyltin iodides, dihydrocarbyltin iodides, trihydrocarbyltin iodides, and tetrahydrocarbyltin compounds. Examples of such organometallic compounds include compounds having the formula:

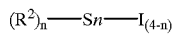

wherein each $R^2$ independently is selected from alkyl or substituted alkyl moieties having up to about 20 carbon atoms, cycloalkyl or substituted cycloalkyl having about 5 to 20 carbon atoms, carbocyclic aryl or substituted carbocyclic aryl having about 6 to 20 carbon atoms, or heteroaryl or substituted heteroaryl moieties having about 4 up to 20 carbon atoms; and n is 1, 2, 3, or 4.

Specific examples of the organometallic compounds include dibutyltin diiodide, tributyltin iodide, trioctyltin iodide, triphenyltin iodide, trimethyltin iodide, butyltin triiodide, tetrabutyltin, tetraoctyltin, triphenyltin iodide, tribenzyltin iodide, dimethyltin diiodide, diphenyltin diiodide, tricyclohexyltin iodide, and dicyclohexyltin diiodide.

The preferred organometallic compounds comprise tin (IV) iodides having the above general formula and a total of about 2 to 36 carbon atoms wherein each $R^2$ substituent independently is selected from alkyl of up to about 12 carbon atoms, benzyl, phenyl, or phenyl substituted with up to 3 substituents selected from lower alkyl, lower alkoxy, or halogen; and n is 2 or 3.

Some of the tetra-alkyl or -aryl substituted tin compounds may react with the alkali metal iodide co-catalyst under the conditions of isomerization to form in situ organotin iodide compounds. Such tetrahydrocarbyltin compounds include tetraphenyltin.

The amount of the organotin component of the novel catalyst compositions of this invention can vary substantially depending on the mode in which the isomerization process is operated, the particular organotin compound and alkali metal iodide present, etc.

The catalyst system is preferably employed in our process as an intimate mixture of one or more of the organotin compounds and one or more of the alkali metal iodides described hereinabove. The organotin compound:alkali metal iodide weight ratio of the catalyst system can vary substantially, e.g., from 200:1 to 1:100, depending on the particular catalyst components selected. The preferred organotin compound:alkali metal iodide weight ratio is about 50:1 to 1:50. Particularly preferred catalyst systems comprise a mixture of one or more of the organotin compounds described hereinabove and lithium iodide, potassium iodide, or sodium iodide.

The organotin compound and alkali metal iodide catalyst system may be used with an inert organic solvent, if desired, to alter the reaction conditions and/or reactor configuration. The optional, inert organic solvent may also be used to assist the catalytic process.

Thus, another embodiment of our invention comprises the isomerization of an epoxyalkene to the corresponding 2,5-dihydrofuran in the presence of a catalyst solution. This embodiment may be carried out in the presence of one or more of the above-described organotin compounds and alkali metal iodides. Accordingly, the catalyst solution preferably comprises a catalytic amount of (i) one or more of the above-described organotin compounds and (ii) one or more of the above-described alkali metal iodides in (iii) an inert organic solvent, i.e., a solvent that does not react with the γ,δ-epoxyalkene or γ,δ-epoxycycloalkene reactants or the 2,5-dihydrofuran products. Examples of the solvents which may be used include aliphatic and aromatic hydrocarbons such as heptane, toluene, specific or mixed xylenes, pseudocumene, and mesitylene; halogenated hydrocarbons such as chlorobenzene, 1,2-dichlorobenzene, and 1,1,2,2-tetrachloroethane; ketones such as cyclohexanone, 5-methyl-2-hexanone, and 2-heptanone; ethers such as 2,5-dihydrofuran, tetrahydrofuran, and bis(2-methoxyethyl) ether; esters such as isobutyl acetate; and tertiary amides such as N-methyl-2-pyrrolidinone, N-cyclohexyl-2-pyrrolidinone, N-ethyl-2-pyrrolidinone, and N,N-dimethylacetamide. Normally, for ease of separation, the solvent or mixture of solvents employed have boiling points at least 20° C. above the boiling point of the 2,5-dihydrofuran product and the unsaturated aldehyde or ketone by-products.

The concentrations of the organotin compound and the alkali metal iodide in the inert, organic solvent can be varied substantially depending, for example, on the particular catalytically-effective components present, the design of the reactor system, etc. Typically, the concentration of the organotin compound will be about 1 to 70 weight percent and the concentration of the alkali metal iodide will be about 1 to 70 weight percent, both concentrations being based on the total weight of the catalyst solution. Normally, the mole ratio of alkali metal iodide to organotin compound is in the range of 50:1 to 1:50.

The preferred catalyst solution comprises:
(i) about 1 to 50 weight percent of an organotin compound containing a total of about 2 to 36 carbon atoms and having the formula:

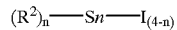

wherein each $R^2$ substituent independently is selected from alkyl of up to about 12 carbon atoms, benzyl, phenyl or phenyl substituted with up to 3 substituents selected from lower alkyl, lower alkoxy, and halogen, and n is 1, 2, 3 or 4;

(ii) about 1 to 50 weight percent of an alkali metal iodide; and (iii) an inert organic solvent selected from tertiary amides such as N-methyl-2-pyrrolidinone, N-cyclohexyl-2-pyrrolidinone, N-ethyl-2-pyrrolidinone, and N,N-dimethylacetamide, with N-alkyl-2-pyrrolidones being particularly preferred.

Some organotin compounds, some alkali metal iodides, and the reaction mixture can be mutually soluble. The reaction mixture can include the epoxyalkene itself and mixtures of epoxyalkene, 2,5-dihydrofuran, epoxyalkene oligomers, and polymers which are formed as a consequence of the reaction. As a result, the addition of an inert organic solvent may not be necessary. This is particularly true when trioctyltin iodide and lithium iodide are used as the catalyst system. Moreover, if desired, a mixture of epoxyalkene with the reaction product 2,5-dihydrofuran and/or the epoxyalkene oligomers and polymers formed in the course of the reaction can be used in combination with, or in lieu of, the inert organic solvent in the reaction from the beginning.

The isomerization process may be carried out using the catalyst solutions described hereinabove by contacting a γ,δ-epoxyalkene or γ,δ-epoxycycloalkene at a temperature of about 50 to 200° C., preferably about 80 to 160° C., depending on the solvent or mixture of solvents employed. The process may be carried out at atmospheric or super-atmospheric pressures, e.g., up to about 22 bar (absolute).

The process employing the catalyst solution may be carried out in a batch, semi-continuous, or continuous mode of operation. For example, batch operation may comprise refluxing a mixture of the γ,δ-epoxyalkene and catalysts, e.g., tributyltin iodide and lithium or potassium iodide, in a solvent such as N-methylpyrrolidone for a time sufficient to convert essentially all of the epoxide to the 2,5-dihydrofuran. The products are then separated by distillation from the mixture. The undistilled catalyst solution may be reused in a subsequent reaction.

The catalyst solution preferably is employed in a continuous mode of operation wherein a γ,δ-epoxyalkene or γ,δ-epoxycycloalkene is added to a recirculated catalyst solution which is then introduced into a continuous reactor. After isomerization, the reaction stream is fed to a distillation system for removal of product or products and recycle of the catalyst solution. Examples of continuous reactor designs in which the process can be performed are continuous stirred tank reactors and plug-flow reactors.

Our novel isomerization process and the catalyst systems, compositions, and solutions useful in practicing the invention are further illustrated by the following examples. The conversions and selectivities reported in the examples were determined by gas chromatographic analyses performed on a Hewlett-Packard 5890 series II gas chromatography.

EXAMPLE 1

To a 100 mL three-neck stirred flask equipped with a distillation head and a thermowell were placed 11.70 g (0.02 mol) of trioctyltin iodide and 8.01 g (0.06 mol) of lithium iodide in 50 g N-methylpyrrolidone. The mixture was heated to 135° C. With a quantity-regulated pump, 10 g of epoxybutene per hour were metered in. At the same time, a mixture of 2,5-DHF and the unreacted epoxybutene was distilled off. After 72 h, 734.9 g of epoxybutene were pumped in and 688.4 g of distillate were obtained. After reducing the pressure to 30 mmHg, another 20.6 g of distillate was obtained. Oligomer (25.9 g) remained in the pot. GC analysis of the combined distillates indicated the following composition:

89.79 wt % 2,5-dihydrofuran;

7.84 wt % epoxybutene; and 2.11 wt % crotonaldehyde.

With a 92.43% conversion, therefore, a selectivity of 93.7% was attained. The formation of oligomers was 3.81%.

For the purpose of evaluating the activity of the catalyst system, samples were taken periodically as distillate for GC analysis. Results are listed in Table 1 which illustrate the relationship of the conversion of epoxybutene to 2,5-dihydrofuran vs. reaction time (excluding the formation of oligomers).

TABLE 1

| Reaction Time (hour) | Conversion to 2,5-DHF (%) |
| --- | --- |
| 1 | 88 |
| 2 | 87 |
| 3.5 | 87 |
| 6 | 87 |
| 7 | 89 |

TABLE 1-continued

| Reaction Time (hour) | Conversion to 2,5-DHF (%) |
| --- | --- |
| 8 | 90 |
| 32 | 89 |
| 55 | 91 |
| 70.5 | 93 |
| 72 | 92 |

As illustrated in Table 1, the catalyst reactivity remains unchanged after 72 hours of reaction run.

EXAMPLE 2

To a 100 mL three-neck stirred flask equipped with a distillation head and a thermowell were placed 5.85 g (0.01 mol) of trioctyltin iodide and 4.05 g (0.03 mol) of lithium iodide in 50 g N-methylpyrrolidone. The mixture was heated to 135° C. With a quantity-regulated pump, 10 g of epoxybutene per hour were metered in. At the same time, a mixture of 2,5-DHF and the unreacted epoxybutene was distilled off. After 71.5 h, 835.88 g of epoxybutene were pumped in and 771.02 g of distillate were obtained. After reducing the pressure to 30 mmHg, another 26.12 g of distillate was obtained. Oligomer (38.74 g) remained in the pot. GC analysis of the combined distillates indicated the following:

85.24 wt % 2,5-dihydrofuran;

13.42 wt % epoxybutene; AND 1.14 wt % crotonaldehyde.

With an 87.20% conversion, therefore, a selectivity of 93.22% was attained. The formation of oligomers was 5.31%.

For the purpose of evaluating the activity of the catalyst system, samples were taken periodically as distillate for GC analysis. Results are listed in Table 2 which illustrate the relationship of the conversion of epoxybutene to 2,5-dihydrofuran vs. reaction time (excluding the formation of oligomers).

TABLE 2

| Reaction Time (hour) | Conversion to 2,5-DHF (%) |
| --- | --- |
| 1 | 85 |
| 2 | 85 |
| 3.5 | 88 |
| 4.5 | 86 |
| 22.5 | 85 |
| 26 | 85 |
| 30 | 84 |
| 46.5 | 83 |
| 55 | 85 |
| 71.5 | 86 |

As illustrated in Table 2, the catalyst reactivity remains unchanged after 72 hours of reaction run.

EXAMPLE 3

To a 100 mL three-neck stirred flask equipped with a distillation head and a thermowell were placed 5.85 g (0.01 mol) of trioctyltin iodide and 4.98 g (0.03 mol) of potassium iodide in 50 g of N-methylpyrrolidone. The mixture was heated to 135° C. With a quantity-regulated pump, 10 g of epoxybutene per hour were metered in. At the same time, a mixture of 2,5-DHF and the unreacted epoxybutene was distilled off. After 76.5 h, 732.5 g of epoxybutene were pumped in and 693.24 g of distillate were obtained. After reducing the pressure to 30 mmHg, another 16.42 g of distillate were obtained. Oligomer (23.06 g) remained in the pot. GC analysis of the combined distillates indicated the following:

84 wt % 2,5-dihydrofuran;

12.75 wt % epoxybutene; and 2.99 wt % crotonaldehyde.

With an 87.65% conversion, therefore, a selectivity of 92.85% was attained. The formation of oligomers was 3.56%.

For the purpose of evaluating the activity of the catalyst system, samples were taken periodically as distillate for GC analysis. Results are listed in Table 3 which illustrate the relationship of the conversion of epoxybutene to 2,5-dihydrofuran vs. reaction time (excluding the formation of oligomers).

TABLE 3

| Reaction Time (hour) | Conversion to 2,5-DHF (%) |
| --- | --- |
| 1 | 89 |
| 2 | 89 |
| 18 | 86 |
| 21 | 86 |
| 25.5 | 86 |
| 42 | 84 |
| 47 | 84 |
| 51 | 81 |
| 70.5 | 80 |
| 76.5 | 80 |

As illustrated in Table 3, the catalyst reactivity slightly decreased after 76 hours of reaction run.

EXAMPLE 4

In a 300 mL Fischer-Porter glass reactor were charged trioctyltin iodide (6.0 g, 0.010 mol), potassium iodide (4.0 g, 0.024 mol), epoxybutene (30 g, 0.43 mol), and N-methylpyrrolidone (50 g). The reactor was purged three times with nitrogen and was pressurized to 20 psig with nitrogen. The reactor was agitated by a magnetic stirrer and heated by an oil bath. The temperature was brought up to 145° C. and held at this temperature for 120 minutes. After cooling to room temperature, the reaction mixtures were analyzed by gas chromatography. GC indicated that all epoxybutene was converted to 2,5-dihydrofuran and crotonaldehyde with selectivity of 96.16% and 3.14%, respectively. Distillation of the reaction mixtures afforded 2,5-dihydrofuran in 89.6% yield. Distillation under high vacuum afforded only 1.6 grams of oligomers.

EXAMPLE 5

To a 100 ml three-neck stirred flask equipped with a distillation head and a thermowell were placed 6.0 g (0.01 mol) of trioctyltin iodide, 4.0 g (0.024 mol) of potassium iodide, and 50 g of N-methylpyrrolidone. The mixture was heated to 135° C. With a quantity-regulated pump, 15 g of epoxybutene per hour was metered in. At the same time, a mixture of 2,5-DHF and the unreacted epoxybutene was distilled off. After 36 hours, a total of 510 g of distillates was collected. GC analysis of the combined distillates indicated the following composition:

86.5 wt % 2,5-dihydrofuran;

7.6 wt % epoxybutene; and 1.2 wt % crotonaldehyde.

The above distillate was fed into the flask containing the same catalyst adducts at 135° C. With the same quantity-regulated pump, 15 g of the above distillate per hour was metered in. At the same time, a mixture of 2,5-dihydrofuran and the unreacted epoxybutene was distilled off. After 25 hours under these conditions, a total of 367 g of distillates was collected. GC analysis of the combined distillates indicated the following composition:

93.6 wt % 2,5-dihydrofuran;

0.9 wt % epoxybutene; and 3.1 wt % crotonaldehyde.

COMPARATIVE EXAMPLE 1

To a 100 mL three-neck stirred flask equipped with a distillation head and a thermowell were placed 5.85 g (0.01 mol) of trioctyltin iodide and 22.53 g (0.03 mol) of trioctyl (octadecyl)phosphonium iodide. The mixture was heated to 135° C. With a quantity-regulated pump, 10 g of epoxybutene per hour were metered in. At the same time, a mixture of 2,5-DHF and the unreacted epoxybutene was distilled off. After 73 h, 695.58 g of epoxybutene were pumped in and 660.09 g of distillate were obtained. After reducing the pressure to 30 mmHg, another 3.69 g of distillate was obtained. Oligomer (31.80 g) remained in the pot. GC analysis of the combined distillates indicated the following:

74.13 wt % 2,5-dihydrofuran;

21.59 wt % epoxybutene; and 4.095 wt % crotonaldehyde.

With a 79.40% conversion, therefore, a selectivity of 89.10% was attained. The formation of oligomers was 5.76%.

For the purpose of evaluating the activity of the catalyst system, samples were taken periodically as distillate for GC analysis. Results are listed in Table C-1 which illustrate the relationship of the conversion of epoxybutene to 2,5-dihydrofuran vs. reaction time (excluding the formation of oligomers).

TABLE C-1

| Reaction Time (hour) | Conversion to 2,5-DHF (%) |
| --- | --- |
| 2 | 68 |
| 4 | 82 |
| 5.5 | 82 |
| 21 | 81 |
| 27.5 | 77 |
| 29.5 | 77 |
| 47 | 76 |
| 54.5 | 73 |
| 71 | 66 |
| 73 | 61 |

As illustrated in Table C-1, the catalyst reactivity noticeably decreased after 73 hours of reaction run.

COMPARATIVE EXAMPLE 2

To a 100 mL three-neck stirred flask equipped with a distillation head and a thermowell were placed 1.89 g (0.01 mol) of $SnCl_2$ and 4.98 g (0.03 mol) of KI in 50 g of N-methylpyrrolidone. The mixture was heated to 135° C. With a quantity-regulated pump, 10 g of epoxybutene per hour were metered in. At the same time, a mixture of 2,5-DHF and the unreacted epoxybutene was distilled off. After 25 h, 258.4 g of epoxybutene were pumped in and 167.89 g of distillate were obtained. After reducing the pressure to 30 mmHg, another 13.57 g of distillate were obtained. Oligomer (76.94 g, 31.61% of reacted EpB) was obtained. GC analysis of the combined distillates indicated the following:

72.26 wt % 2,5-dihydrofuran;

8.32 wt % epoxybutene;

10.44 wt % crotonaldehyde; and 8.97 wt % other low boilers.

With a 94.2% conversion, therefore, a selectivity of 53.87% was attained. Oligomer formation was 31.61%.

For the purpose of evaluating the activity of the catalyst system, samples were taken periodically as distillate for GC analysis. Results are listed in Table C-2 which illustrate the relationship of the conversion of epoxybutene to 2,5-dihydrofuran vs. reaction time (excluding the formation of oligomers).

TABLE C-2

| Reaction Time (hour) | Conversion to 2,5-DHF (%) |
|---|---|
| 1 | 91 |
| 2 | 87 |
| 3 | 84 |
| 4 | 80 |
| 5 | 76 |
| 7 | 74 |
| 8 | 69 |
| 23.5 | 63 |
| 25 | 63 |

As illustrated in Table C-2, the catalyst reactivity decreased rapidly just after 25 hours of reaction run.

COMPARATIVE EXAMPLE 3

To a 100 mL three-neck stirred flask equipped with a distillation head and a thermowell were placed 2.49 g (0.01 mol) of $Bu_2SnO$ and 4.98 g (0.03 mol) of KI in 50 g of N-methylpyrrolidone. The mixture was heated to 135° C. With a quantity-regulated pump, 10 g of epoxybutene per hour were metered in. At the same time, a mixture of 2,5-DHF and the unreacted epoxybutene was distilled off. After 8.33 h, 63.6 g of epoxybutene were pumped in and 61.72 g of distillate were obtained. After reducing the pressure to 30 mmHg, another 6 g of distillate were obtained. Oligomer (1.88 g) remained in the pot. GC analysis of the combined distillates indicated the following:

1.42 wt % 2,5-dihydrofuran;

96.69 wt % epoxybutene; and 1.89 wt % crotonaldehyde.

With a 6.16% conversion, therefore, a selectivity of 22.45% was attained. Oligomer formation was 47.96%.

For the purpose of evaluating the activity of the catalyst system, samples were taken periodically as distillate for GC analysis. Results are listed in Table C-3 which illustrate the relationship of the conversion of epoxybutene to 2,5-dihydrofuran vs. reaction time (excluding the formation of oligomers).

TABLE C-3

| Reaction Time (hour) | Conversion to 2,5-DHF (%) |
|---|---|
| 2 | 1.55 |
| 4 | 1.36 |
| 8.33 | 1.34 |

As illustrated in Table C-3, the catalyst reactivity is extremely low.

COMPARATIVE EXAMPLE 4

To a 100 mL three-neck stirred flask equipped with a distillation head and a thermowell were placed 3.19 g (0.01 mol) of zinc iodide, 4.98 g (0.03 mol) of potassium iodide, and 7.97 g of 18-crown-6. The mixture was heated to 135° C. With a quantity-regulated pump, 10 g of epoxybutene per hour were metered in. At the same time, a mixture of 2,5-DHF and the unreacted epoxybutene was distilled off. After 29.25 h, 370.42 g of epoxybutene were pumped in and 325.36 g of distillate were obtained. Oligomer (45.69 g) remained in the pot. GC analysis of the combined distillates indicated the following:

31.02 wt % 2,5-dihydrofuran;

64.74 wt % epoxybutene; and 3.72 wt % crotonaldehyde.

With a 43.13% conversion, therefore, a selectivity of 63.16% was attained. The formation of oligomers was 28.60%.

For the purpose of evaluating the activity of the catalyst system, samples were taken periodically as distillate for GC analysis. Results are listed in Table C-4 which illustrate the relationship of conversion of epoxybutene to 2,5-dihydrofuran vs. reaction time (excluding the formation of oligomers).

TABLE C-4

| Reaction Time (hour) | Conversion to 2,5-DHF (%) |
|---|---|
| 1 | 42 |
| 2 | 41 |
| 3 | 26 |
| 4.25 | 27 |
| 6.25 | 28 |
| 7.75 | 27 |
| 23.25 | 34 |
| 26.25 | 33 |
| 28.25 | 33 |
| 29.25 | 34 |

As illustrated in Table C-4, the catalyst reactivity was very low.

COMPARATIVE EXAMPLE 5

To a 100 mL three-neck stirred flask equipped with a distillation head and a thermowell were placed 3.19 g (0.01 mol) of zinc iodide and 4.98 g (0.03 mol) of potassium iodide in 50 g of N-methylpyrrolidone. The mixture was heated to 135° C. With a quantity-regulated pump, 10 g of epoxybutene per hour were metered in. At the same time, a mixture of 2,5-DHF and the unreacted epoxybutene was distilled off. After 25.25 h, 265.55 g of epoxybutene were pumped in and 209.47 g of distillates were obtained. After reducing the pressure to 30 mmHg, another 6.5 g of distillate were obtained. Oligomer (49.58 g) remained in the pot. GC analysis of the combined distillates indicated the following:

83.7 wt % 2,5-dihydrofuran;

14.18 wt % epoxybutene; and 1.43 wt % crotonaldehyde.

With an 88.85% conversion, therefore, a selectivity of 76.62% was attained. The formation of oligomers was 21.01%.

For the purpose of evaluating the activity of the catalyst system, samples were taken periodically as distillate for GC analysis. Results are listed in Table C-5 which illustrate the relationship of conversion of epoxybutene to 2,5-dihydrofuran vs. reaction time (excluding oligomer formations).

TABLE C-5

| Reaction Time (hour) | Conversion to 2,5-DHF (%) |
|---|---|
| 1 | 87 |
| 3 | 86 |
| 4 | 87 |
| 4.67 | 87 |
| 21 | 78 |
| 23 | 78 |
| 25 | 75 |
| 25.5 | 71 |

As illustrated in Table C-5, the catalyst reactivity decreased rapidly just after 25.5 hours of reaction run.

COMPARATIVE EXAMPLE 6

In a 300 mL Fischer-Porter glass reactor were charged zinc iodide (3.0 g, 0.009 mol), potassium iodide (1.0 g, 0.006 mol), aluminum acetylacetonate (1.9 g, 0.006 mol), epoxybutene (30 g, 0.43 mol), hydrogen iodide (2.0 g, 0.009 mol), and N-methylpyrrolidone (120 g). The reactor was purged three times with nitrogen and was pressurized to 20 psig with nitrogen. The reactor was agitated by a magnetic stirrer and heated by an oil bath. The temperature was brought up to 120° C. and held at this temperature for 90 minutes. After cooling to room temperature, the reaction mixtures were analyzed by gas chromatography. GC indicated that all epoxybutene was consumed. Distillation of reaction mixtures afforded 2,5-dihydrofuran (16.3 g, 54% yield) and crotonaldehyde (1.5 g, 5%). Distillation under high vacuum afforded 10.2 grams of oligomer (34%).

The invention has been described in detail with particular reference to examples and preferred embodiments thereof, but it will be understood that variations and modifications can be effected within the spirit and scope of the invention.

We claim:

1. A process for the isomerization of γ,δ-epoxyalkenes or γ,δ-epoxycycloalkenes to 2,5-dihydrofurans, which process comprises contacting a γ,δ-epoxyalkene or γ,δ-epoxycycloalkene with a catalytic amount of an organotin (IV) compound selected from hydrocarbytin iodides, dihydrocrbyltin iodides, trihydrocarbyltin iodides, and tetrahydrocarbytin compounds in combination with an alkali metal iodide at conditions effective to produce a 2,5-dihydrofuran compound.

2. The process according to claim 1, wherein the γ,δ-epoxyalkene or γ,δ-epoxycycloalkene has the following structural formula (I):

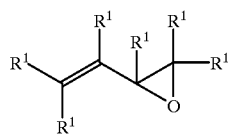

(I)

wherein each $R^1$ is independently selected from hydrogen, alkyl of up to about 8 carbon atoms, a carbocyclic or heterocyclic aryl group of about 5 to 10 carbon atoms or halogen, or any two $R^1$ substituents collectively may represent an alkylene group forming a ring containing in the main chain up to about 8 carbon atoms.

3. The process according to claim 1, wherein the γ,δ-epoxyalkene or γ,δ-epoxycycloalkene is 3,4-epoxy-3-methyl-1-butene, 2,3-dimethyl-3,4-epoxy-1-butene, 3,4-epoxycyclooctene, 3,4-epoxy-1-butene, or 2,5-dimethyl-2,4-hexadiene monoepoxide.

4. The process according to claim 1, wherein the alkali metal iodide is lithium iodide, sodium iodide, or potassium iodide.

5. The process according to claim 1, wherein the organotin compound is dibutyltin diiodide, tributyltin iodide, trioctyltin iodide, triphenyltin iodide, trimethyltin iodide, butyltin triiodide, tetrabutyltin, tetraoctyltin, triphenyltin iodide, tribenzyltin iodide, dimethyltin diiodide, diphenyltin diiodide, tricyclohexyltin iodide, or dicyclohexyltin diiodide.

6. The process according to claim 1, wherein a 50:1 to 1:50 weight ratio of organotin compound:alkali metal iodide is used.

7. The process according to claim 1, which is carried out in the presence of an added inert organic solvent.

8. The process according to claim 7, wherein the inert organic solvent is heptane, toluene, xylene, pseudocumene, mesitylene, chlorobenzene, cyclohexanone, 5-methyl-2-hexanone, 2-heptanone, 2,5-dihydrofuran, tetrahydrofuran, bis-(2-methoxyethyl)ether, isobutyl acetate, N-methyl-2-pyrrolidinone, N-cyclohexyl-2-pyrrolidinone, N-ethyl-2-pyrrolidinone, N,N-dimethylacetamide, or mixtures thereof.

9. The process according to claim 1, which is carried out in the absence of an added inert organic solvent.

10. A process for the preparation of 2,5-dihydrofurans of the structural formula (II):

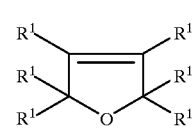

(II)

wherein each $R^1$ is independently selected from hydrogen, alkyl of up to about 8 carbon atoms, a carbocyclic or heterocyclic aryl group of about 5 to 10 carbon atoms or halogen, or any two $R^1$ substituents collectively may represent an alkylene group forming a ring containing in the main chain up to about 8 carbon atoms, which process comprises contacting an γ,δ-epoxyalkene or γ,δ-epoxycycloalkene of the structural formula (I):

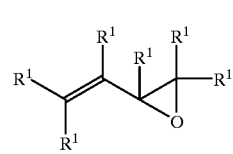

(I)

wherein $R^1$ is as defined above, with a catalyst system comprising an organotin (IV) compound selected from hydrocarbytin iodides, dihydrocrbyltin iodides, trihydrocarbyltin iodides, and tetrahydrocarbytin compounds and an alkali metal iodide at a temperature of 50° to 200° C.

11. The process according to claim 10, which is carried out in the absence of an added inert organic solvent.

12. The process according to claim 10, wherein the catalyst system is in the form of a solution.

13. The process according to claim 12, wherein the solution further comprises an inert organic solvent selected from N-methyl-2-pyrrolidinone, N-cyclohexyl-2-pyrrolidinone, N-ethyl-2-pyrrolidinone, and N,N-dimethylacetamide.

14. The process according to claim 10, wherein the organotin compound has the formula

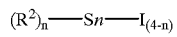

wherein each $R^2$ independently is selected from alkyl of up to about 12 carbon atoms, benzyl, phenyl or phenyl substituted with up to 3 substituents selected from lower alkyl, lower alkoxy, and halogen, and n is 1, 2, 3 or 4.

15. The process according to claim 10, wherein the alkali metal iodide is lithium iodide, potassium iodide, or sodium iodide.

16. A process for the preparation of 2,5-dihydrofuran, which process comprises contacting 3,4-epoxy-1-butene with a catalyst system comprising an organotin iodide and an alkali metal iodide at conditions effective produce 2,5-dihydrofuran.

17. The process according to claim 16, wherein the organotin iodide is trioctyltin iodide and the alkali metal iodide is lithium iodide.

18. The process according to claim 16, wherein the organotin iodide is trioctyltin iodide and the alkali metal iodide is potassium iodide.

19. The process according to claim 16, which is carried out in the presence of N-methylpyrrolidone.

20. The process according to claim 16, which is carried out in the absence of an added inert organic solvent.

21. A process for the isomerization of γ,δ-epoxyalkenes or γ,δ-epoxycycloalkenes to 2,5-dihydrofurans, which process comprises contacting a γ,δ-epoxyalkene or γ,δ-epoxycycloalkene with a catalyst system consisting essentially of an organotin compound and an alkali metal iodide at conditions effective to produce a 2,5-dihydrofuran compound.

22. The process according to claim 21, wherein the γ,δ-epoxyalkene or γ,δ-epoxycycloalkene has the following structural formula (1):

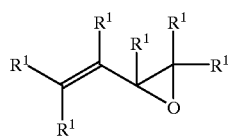

(I)

wherein each $R^1$ is independently selected from hydrogen, alkyl of up to about 8 carbon atoms, a carbocyclic or heterocyclic aryl group of about 5 to 10 carbon atoms or halogen, or any two $R^1$ substituents collectively may represent an alkylene group forming a ring containing in the main chain up to about 8 carbon atoms.

23. The process according to claim 21, wherein the γ,δ-epoxyalkene or γ,δ-epoxycycloalkene is 3,4-epoxy-3-methyl-1-butene, 2,3-dimethyl-3,4-epoxy-1-butene, 3,4-epoxycyclooctene, 3,4-epoxy-1-butene, or 2,5-dimethyl-2,4-hexadiene monoepoxide.

24. The process according to claim 21, wherein the alkali metal iodide is lithium iodide, sodium iodide, or potassium iodide.

25. The process according to claim 21, wherein the organotin compound is selected from hydrocarbyltin iodides, dihydrocarbyltin iodides, trihydrocarbyltin iodides, and tetrahydrocarbyltin compounds.

26. The process according to claim 26, wherein the organotin compound is dibutyltin diiodide, tributyltin iodide, trioctyltin iodide, triphenyltin iodide, trimethyltin iodide, butyltin triiodide, tetrabutyltin, tetraoctyltin, triphenyltin iodide, tribenzyltin iodide, dimethyltin diiodide, diphenyltin diiodide, tricyclohexyltin iodide, or dicyclohexyltin diiodide.

27. The process according to claim 21, wherein a 50:1 to 1:50 weight ratio of organotin compound:alkali metal iodide is used.

28. The process according to claim 21, which is carried out in the presence of an added inert organic solvent.

29. The process according to claim 28, wherein the inert organic solvent is heptane, toluene, xylene, pseudocumene, mesitylene, chlorobenzene, cyclohexanone, 5-methyl-2-hexanone, 2-heptanone, 2,5-dihydrofuran, tetrahydrofuran, bis-(2-methoxyethyl)ether, isobutyl acetate, N-methyl-2-pyrrolidinone, N-cyclohexyl-2-pyrrolidinone, N-ethyl-2-pyrrolidinone, N,N-dimethylacetamide, or mixtures thereof.

30. The process according to claim 21, which is carried out in the absence of an added inert organic solvent.

* * * * *

UNITED STATES PATENT AND TRADEMARK OFFICE
CERTIFICATE OF CORRECTION

PATENT NO. : 6,335,455 B1
DATED : January 1, 2002
INVENTOR(S) : Shaowo Liang et al.

It is certified that error appears in the above-identified patent and that said Letters Patent is hereby corrected as shown below:

Column 11,
Line 42, change "hydrocarbytin" to -- hydrocarbyltin --.
Lines 42-43, change "dihydrocrbyltin" to -- dihydrocarbyltin --.
Lines 43-44, change "tetrahydrocarbytin" to -- tetrahydrocarbyltin --.

Column 12,
Line 56, change "hydrocarbytin" to -- dihydrocarbyltin --.
Line 57, change "tetrahydrocarbytin" to -- tetrahydrocarbyltin --.

Column 14,
Line 21, change "26" to -- 25 --.

Signed and Sealed this

Thirtieth Day of July, 2002

Attest:

JAMES E. ROGAN
*Attesting Officer*   *Director of the United States Patent and Trademark Office*